United States Patent
Zare et al.

[11] Patent Number: 6,136,187
[45] Date of Patent: *Oct. 24, 2000

[54] SEPARATION COLUMN CONTAINING POROUS MATRIX AND METHOD OF PACKING COLUMN

[75] Inventors: Richard N. Zare, Stanford; Maria T. Dulay, Sunnyvale; Rajan P. Kulkarni, Loma Linda, all of Calif.

[73] Assignee: The Board of Trustees of the Leland Stanford Junior University, Stanford, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/987,287

[22] Filed: Dec. 9, 1997

[51] Int. Cl.$^7$ ................................................ B01D 15/08
[52] U.S. Cl. ...................... 210/198.2; 210/656; 96/101
[58] Field of Search ............................... 210/198.2, 635, 210/656, 659; 95/83, 88; 96/101

[56] References Cited

U.S. PATENT DOCUMENTS

| | | | |
|---|---|---|---|
| 3,503,712 | 3/1970 | Sussman | 210/198.2 |
| 3,568,840 | 3/1971 | Hashimoto | 210/198.2 |
| 3,757,490 | 9/1973 | Ma | 210/198.2 |
| 3,808,125 | 4/1974 | Good | 210/198.2 |
| 3,878,092 | 4/1975 | Fuller | 210/198.2 |
| 4,675,300 | 6/1987 | Zare et al. | 436/172 |
| 5,116,495 | 5/1992 | Prohaska | 210/198.2 |
| 5,135,627 | 8/1992 | Soane | 204/182.8 |
| 5,308,495 | 5/1994 | Avnir | 210/198.2 |
| 5,316,680 | 5/1994 | Frechet | 210/198.2 |
| 5,334,310 | 8/1994 | Frechet | 210/198.2 |
| 5,453,185 | 9/1995 | Frechet et al. | 210/198.2 |
| 5,522,994 | 6/1996 | Frechet | 210/198.2 |
| 5,599,445 | 2/1997 | Betz | 210/198.2 |
| 5,637,135 | 6/1997 | Ottenstein et al. | 96/101 |
| 5,647,979 | 7/1997 | Liao | 210/198.2 |
| 5,667,674 | 9/1997 | Hanggi | 210/198.2 |
| 5,719,322 | 2/1998 | Lansbarkis | 210/198.2 |
| 5,728,296 | 3/1998 | Hjerten | 210/198.2 |
| 5,728,457 | 3/1998 | Frechet | 210/198.2 |
| 5,759,405 | 6/1998 | Anderson | 210/198.2 |
| 5,772,875 | 6/1998 | Pettersson | 210/198.2 |
| 5,858,241 | 1/1999 | Dittman | 210/198.2 |

FOREIGN PATENT DOCUMENTS

| | | | |
|---|---|---|---|
| 0439318A2 | 7/1991 | European Pat. Off. | 210/198.2 |
| 0779512A1 | 6/1997 | European Pat. Off. | 210/198.2 |

OTHER PUBLICATIONS

Snyder Introduction to Modern Liquid Chromatography John Wiley & Sons, Inc, New York, 1979, pp. 145–147.

"Preparation and Characterization of Monolithic Porous Capillary Columns Loaded with Chromatographic Particles," M. Dulay et al., *Anal. Chem.* vol. 70, No. 23, Dec. 1, 1998, pp. 5103–5107.

Modification of the Inner Capillary Surface by the Sol–Gel Method: Application to Open Tubular Electrochromatography, Y. Guo et al. *J. Microcolumn Separations*, 7(5), 1995, pp. 485–491.

(List continued on next page.)

*Primary Examiner*—Ernest G. Therkorn
*Attorney, Agent, or Firm*—Majestic, Parsons, Siebert & Hsue P.C.

[57] ABSTRACT

A mixture of chromatographic particles and a solution of water, alcohol and metal alkoxide may be injected by means of a syringe into a capillary column as a gel. The volatile components in the gel are evaporated by means of heating and gas pressure reduction to form a porous sol-gel glass matrix attached to the inner wall of the separation channel. The pores are large enough for the passage of protons, neutral and ionic species but are too small to permit significant leaching of the chromatographic particles. The separation column so formed requires no frits to maintain the glass matrix in place in the column. Electrical potential difference and/or pressure difference may be applied to cause fluid flow in the separation column to cause electrophoretic and chromatographic separation.

29 Claims, 3 Drawing Sheets

OTHER PUBLICATIONS

"Hydrolytically stable amino–silica glass coating material for manipulation of the electroosmotic flow in capillary electrophoresis," Y. Guo et al., *Journal of Chromatography A*, 744, Sep. 13, 1996, pp. 17–29.

"Impregnation of a pH–Sensitive Dye Into Sol–Gels for Fibre Optic Chemical Sensors," G.F. Badini et al., *Analyst*, vol. 120, Apr. 1995, pp. 1025–1028.

"Microporous Polyacrylamide/Poly (ethylene glycol) Matrixes as Stationary Phases in Capillary Electrochromatography," A. Palm et al., *Anal. Chem.*, vol. 69, No. 22, Nov. 15, 1997, pp. 4499–4507.

Automated capillary electrochromatography: reliability and reproducibility studies, M.T. Dulay et al., *Journal of Chromatography A*, 725, Sep. 2, 1996, pp. 361–366.

"Sol–Gel Coating Technology for the Preparation of Solid–Phase Microextraction Fibers of Enhanced Thermal Stability," S.L Chong et al., *Analytical Chemistry*, vol. 69, No. 19, Oct. 1, 1997, pp. 3889–3898.

"On The Limiting Pore Size of Hydrophilic Gels For Electrophoresis and Isoelectric Focusing," P.G. Righetti et al., *J. Biochem. Biophys. Methods*, 1981, No. 4, pp. 347–363.

"'Laterally aggregated'polyacrylamide gels for electrophoresis," P.G. Righetti et al., *Electrophoresis*, No. 13, Sep./Oct. 1992, pp. 587–595.

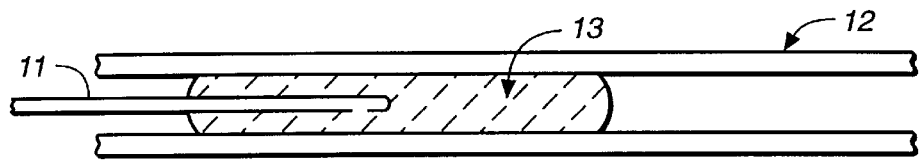
FIG._1
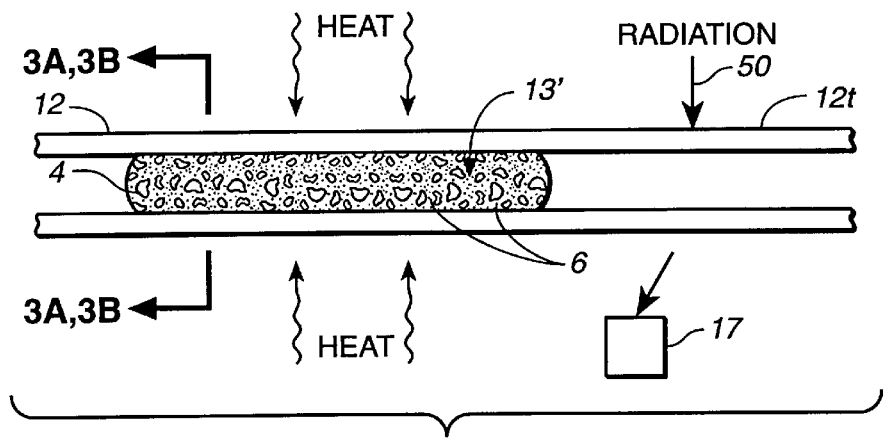
FIG._2
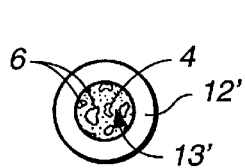
FIG._3A
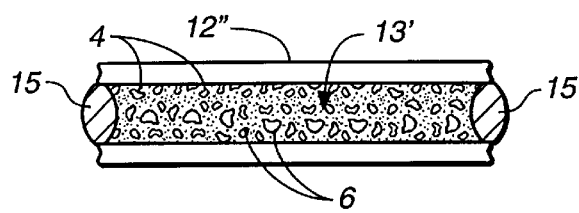
FIG._3B

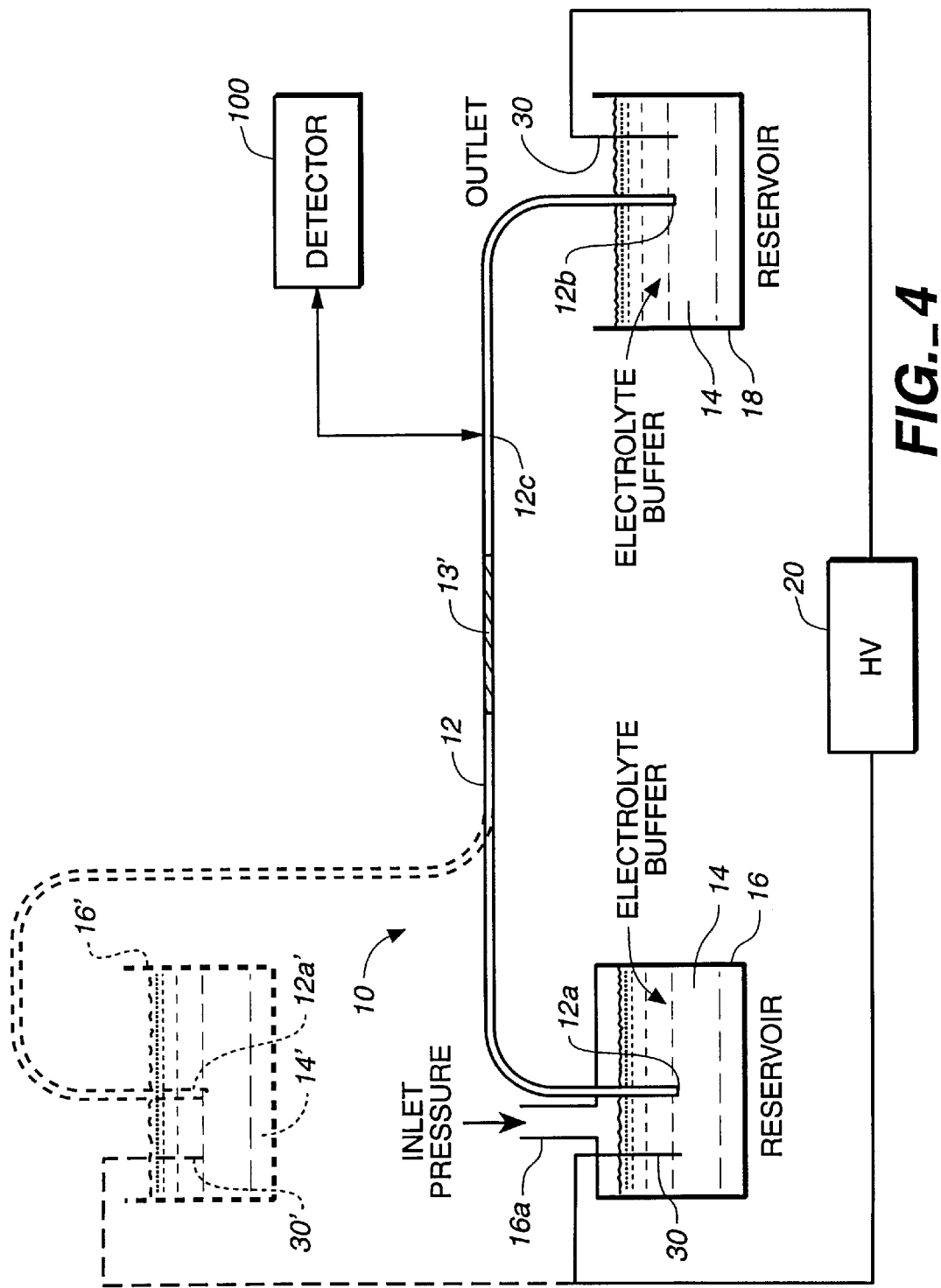
FIG._4

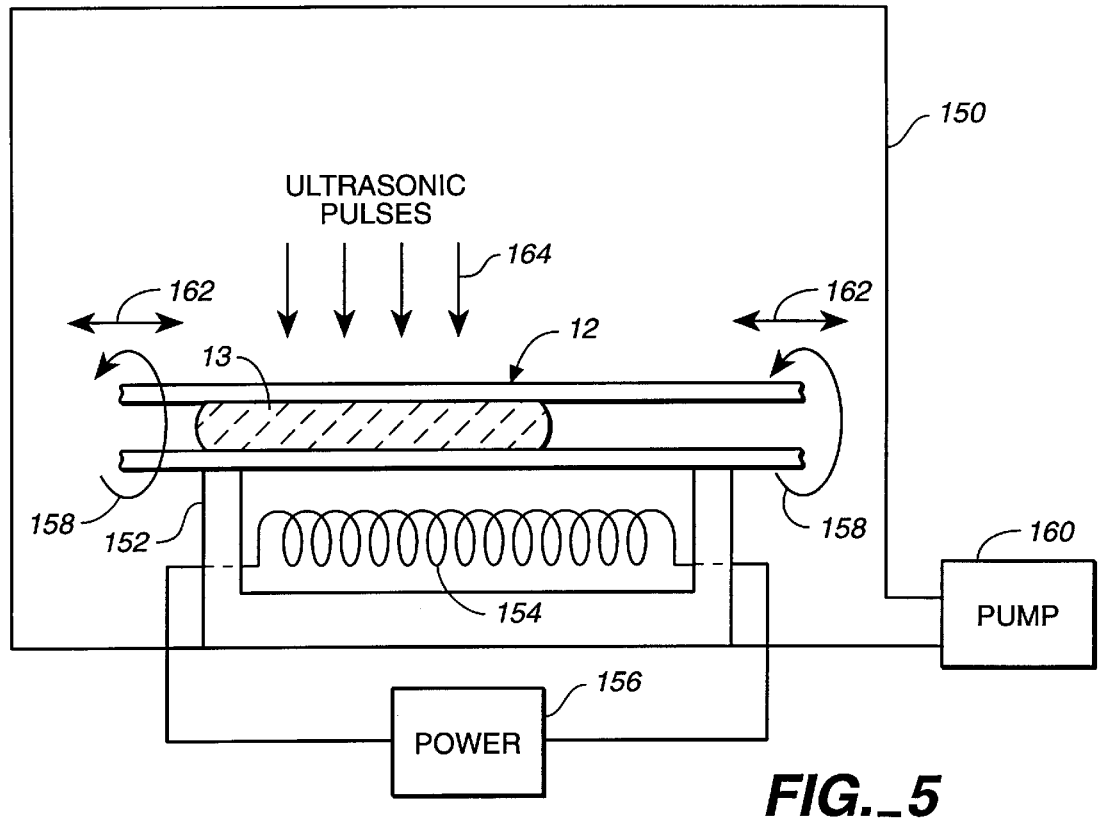
FIG._5
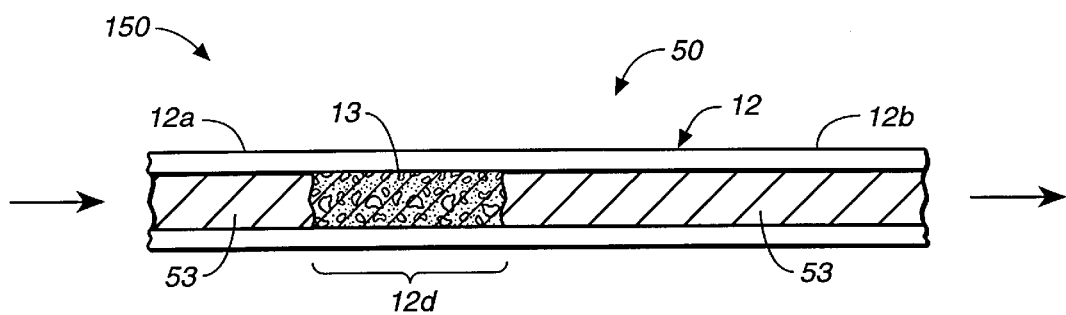
FIG._6

SEPARATION COLUMN CONTAINING POROUS MATRIX AND METHOD OF PACKING COLUMN

BACKGROUND OF THE INVENTION

The invention relates to a separation system employing a column containing a porous matrix embedded with chromatographic particles and a method of packing a channel with the matrix to make the column.

Capillary zone electrophoresis (CZE), with its high peak capacity (i.e., the number of peaks separated per unit time), has long been proven to be an attractive analytical technique for separating ionic species by their electrophoretic mobilities. The separation of neutral species via CZE, however, has remained more problematic. To improve the separation of neutral species via capillary electrophoresis, the technique of capillary electrochromatography (CEC) has been employed, which is a promising technique that seeks to combine the advantages of capillary electrophoresis and chromatography as described in the article by M. T. Dulay et al. in *Chromatogr. A.*, 725 (1996) pp. 361–365).

In CEC, the separation of uncharged analytes is based on partitioning of chromatographic particles such as octadecylsilica, while the separations of charged analytes are based on both partitioning and electrophoretic mobility. Existing techniques for the preparation of packed capillary columns are based on either a slurry packing method or an electrokinetic packing method of small-bore capillary columns. The electrokinetic packing method may be more advantageous than a slurry packing method for the preparation of packed capillary columns with micron-sized inner diameters. Disadvantages of the electrokinetic packing method include the limited choices of chromatographic phases (i.e., only charged particles can be used) and the need for both inlet and outlet frits to prevent the chromatographic particles from leaving the capillary column. This causes the columns to be difficult and time consuming to make.

It is therefore desirable to provide a separation column with improved characteristics and that are easy to make.

SUMMARY OF THE INVENTION

One aspect of the invention is directed towards a separation column comprising a separation channel having a channel wall and a separation medium in the channel. The medium includes a porous matrix attached to the channel wall and chromatographic particles embedded in the matrix forming a packed channel. The channel has no frit therein adjacent to the separation medium.

Another aspect of the invention is directed towards an apparatus for separating a sample into its components, comprising a separation channel having a channel wall; a separation medium in the channel, and means for causing a fluid containing a sample present in a channel to flow and the sample to separate. The medium includes a porous matrix attached to the channel wall and chromatographic particles embedded in the matrix, forming a packed channel. The channel has no frit therein adjacent to the separation medium.

One more aspect of the invention is directed towards a method for making a separation column, comprising introducing a mixture of chromatographic particles and a solution of a monomer and a cross-linking reagent into a separation channel, such channel having a wall; and causing the mixture to form a porous matrix attached to the channel wall with said particles embedded therein.

BRIEF DESCRIPTION OF THE DRAWINGS

FIG. 1 is a partially cross-sectional and partially schematic view of a section of a separation column along a longitudinal axis of the column and of a needle portion of a syringe for injecting a mixture of chromatographic particles and a solution of water, alcohol and a metal alkoxide into the column to illustrate a preferred embodiment of the invention.

FIG. 2 is a cross-sectional view of a portion of the column of FIG. 1 along a longitudinal axis of the column, where the volatile components in the mixture injected into the column have been removed to form a porous sol-gel with chromatographic particles embedded therein to illustrate the invention.

FIGS. 3A and 3B are cross-sectional views of the separation column shown in FIG. 2 along the line 3A, 3B–3A, 3B in FIG. 2 to illustrate two different embodiments of the separation column.

FIG. 4 is a partially schematic and partially cross-sectional view of a separation system employing the separation column of FIG. 2 to illustrate a preferred embodiment of the invention.

FIG. 5 is a schematic view of a system for making the separation column of FIG. 2.

FIG. 6 is a cross-sectional view of a portion of a separation column along a longitudinal axis of the column to illustrate another embodiment of the column and an alternative method for packing the column.

For simplicity in description, identical components are labeled by the same numerals in this application.

DETAILED DESCRIPTION OF THE PREFERRED EMBODIMENTS

In the preferred embodiment, this invention employs a metal alkoxide sol-gel process. The metal alkoxide sol-gel process is a method of preparing metal oxide glasses by hydrolyzing a solution of water, alcohol, and a metal alkoxide source. The sources of these metal oxides, or silanes, are the alkoxy compounds of type $R_nSi(OR')_{4-n}$ as described by C. J. Brinker et al. in *Sol-Gel Science*, Academic Press, Inc., New York, N.Y., 1990. The most commonly used of these compounds is tetraethylorthosilicate (TEOS, $Si(OC_2H_5)_4$), although other compounds such as titanates, and zirconates may also be used for this invention. As these substances polymerize, gelation of the solution occurs. If the volatile solvents in the wet gel are allowed to evaporate, the gel shrinks and hardens, creating a hard porous glass.

Since sol-gel glasses are formed from solution, other molecules can be embedded inside the pores or inside the cavities created. When the solvent evaporates from the gel, the glass that is created is porous. The porosity of the glass allows for the diffusion of protons (and other neutral or ionic species) through the channels. These pores, however, must be large enough to allow species diffusion, but small enough that significant amounts of chromatographic materials cannot leave the xerogel matrix.

FIG. 1 is a partially cross-sectional and partially schematic view of a portion of a separation column 12 along a longitudinal axis of the column and a needle portion 11 of a syringe (not shown) injecting a mixture 13 of chromatographic particles and a solution to illustrate the preferred embodiment of the invention. As shown in FIG. 1, a needle portion 11 is used to inject into a channel within a tube 12, a mixture 13 of chromatographic particles in a solution of water, alcohol and a metal alkoxide. This mixture forms a wet gel 13 in tube 12. After the volatile solvents in the wet gel 13 have evaporated, the gel 13 shrinks and hardens, creating a hard porous glass 13' shown in FIG. 2.

FIG. 2 is a cross-sectional view of column 12 along a longitudinal axis of the column and the hard porous glass 13' in the column resulting from evaporation of the volatile solvents in the wet gel 13 of FIG. 1. As shown in FIG. 2, glass 13' includes pores 4 and chromatographic particles 6 embedded therein. As noted above, the porosity of the glass 13' allows for the diffusion of protons and other neutral or ionic species, but small enough that significant amounts of chromatographic particles 6 cannot leave the glass matrix 13'. Glass 13' forms a secure bond to the inner wall of the tube 12, so that no frit is required adjacent to the glass 13' to maintain the matrix glass 13' in place in tube 12. While pores 4 are big enough to allow diffusion of protons, neutral and ionic species, they are too small for most of the chromatographic particles 6. This prevents leaching of the particles when a fluid is passed through the glass matrix. Thus, when a sample is carried by fluid through glass 13', the sample components will interact with the chromatographic particles 6 and become partitioned or separated.

Tube 12 can have many different cross-sections, such as a circular cross-section shown in FIG. 3A, the cross-section being normal to a longitudinal axis of the tube, shown as tube 12'. Alternatively, tube 12 can have an elongated cross-section as shown in FIG. 3B, where the tube is formed by two flat plates 12" where the tube is formed by sealing the adjacent edges of the two plates by means of an adhesive 15. Such and other cross-sections are possible for tube 12 and are within the scope of the invention. In some embodiments, the internal dimension of tube or channel 12 may range from about 5 to about 3,000 microns. Where tube 12 is a capillary, its internal dimension may range from about 5 to about 300 microns.

Chromatographic particles 6 may comprise uniformly sized particles of the same type, or a mixture of different types of particles of different sizes. Preferably, the particles are of dimensions greater than 0.2 microns.

FIG. 4 is a partially schematic and partially cross-sectional view of a separation system employing a column 12 to illustrate the preferred embodiment of the invention. As shown in FIG. 4, the inlet end 12a of the column is immersed in an electrolyte buffer 14 contained in a reservoir 16. The outlet end 12b is immersed in an electrolyte buffer in reservoir 18. An electrical potential of several kilovolts is applied by high voltage source 20 through electrodes 30 between electrolyte buffer 14 in input and output reservoirs 16, 18, causing a potential difference and electric field along the column 12. Such potential difference causes an electroosmotic flow in tube 12 from reservoir 16 towards reservoir 18. A sample may be introduced into inlet 12a by means known to those skilled in the art, such as by gravity or by electrokinetic injection. Such sample would be caused to separate in tube 12 due to electrophoresis. In addition, the interaction between the sample components (which may be uncharged or neutral electrically) and the chromatographic particles 6 in the glass matrix 13' causes chromatographic separation of the components as well.

Instead of, or in addition to, the use of electrical potential to cause fluid flow in column 12, the fluid flow can also be caused by applying a pressure differential along the column 12, which, in addition to or instead of the electric field applied along the column, causes fluid flow from reservoir 16 to reservoir 18. This can be performed by using an enclosed reservoir 16 except for an inlet 16a, through which gas pressure is applied as shown in FIG. 4. The gas pressure may be supplied by means of a pump (not shown) for example. The gas pressure applied through inlet 16a causes buffer 14 to be pushed downward and the buffer to flow into the inlet 12a and column 12 to reservoir 18. Instead of using a pump to apply a pressure differential in column 12, a pressure differential may also be applied by raising the column inlet 12a to a position 12a' at an elevation higher than the outlet end 12b of the column, as shown in dotted lines in FIG. 4. Thus, as shown in dotted lines, the new positions of the inlet 12a' of the column, of reservoir 16' containing buffer 14' and electrode 30' immersed in the buffer in reservoir 16' are all at elevations above the outlet end 12b of the column. Alternatively, instead of raising the inlet end 12a, the same goal can be achieved by lowering outlet end 12b of the tube, by lowering reservoir 18, electrode 30 in such reservoir and end 12b. Or, the pressure in reservoir 18 can be reduced by means of a pump (not shown) to one below that of reservoir 16 to achieve a pressure differential between ends 12a, 12b, and to create fluid flow in tube 12.

In the embodiment of FIG. 2, only a portion of the column 12 is filled with the porous glass with chromatographic particles embedded therein, and the remaining portion of the column is not filled with the porous glass. In an arrangement similar to that in prior detection schemes, the separated sample components may be detected optically, such as by laser induced fluorescence as described in U.S. Pat. No. 4,675,300 in a transparent column portion 12t that is transparent to radiation and downstream from glass 13' as shown in FIGS. 2 and 4. As shown in FIG. 2, the portion 12t does not contain any of the chromatographic particles present in glass matrix 13' and transmits radiation without significant scattering, such as UV or visible light. The sample components passing through such portion 12t may be illuminated by means of radiation along arrow 50 to induce fluorescence, where the induced fluorescence may be detected by means of a detector 17 preferably placed away from the path of radiation 50. This is shown schematically in FIG. 4, where a detector 100 detects the separated sample components at location 12c. When detector 100 detects the sample components by means of laser induced fluorescence, the sample components may need to be first tagged by means of a fluorophore and detector 100 includes a laser source as well as a photodetector.

In order to facilitate the evaporation of the volatile solvents in mixture 13 in FIG. 1, the tube 12 containing mixture 13 may be placed in an oven chamber 150 as shown in FIG. 5. Tube 12 is supported by a pedestal 152 in the oven chamber and heat is applied by a heating coil 154 through which a current is passed by means of a power supply 156. To further facilitate the evaporation of volatile solvents, the gas pressure in oven chamber 150 is reduced by means of a pump 160. While both heating and reduction of gas pressure may be used together to accelerate the evaporation of volatile solvents, heating may be used without pressure reduction and vice versa; all such variations are within the scope of the invention. When the volatile solvents have evaporated, mixture 13 then forms a porous sol-gel glass that is attached securely to the inner walls of tube 12, with the chromatographic particles 6 embedded therein. It has been found that in some instances, a hardened porous sol-gel glass may form in about 24 hours.

To achieve a more uniform distribution of the chromatographic particles in the sol-gel, it may be desirable to agitate the mixture 13 when the volatile components are escaping from the mixture. This can be done for example by rotating the tube along arrows 158, shaking the tube along arrows 162, or supplying ultrasonic pulses along arrows 164 from an ultrasonic source (not shown) as shown in FIG. 5 in a manner known to those skilled in the art.

With this monolithic packing method, chromatographic materials that are charged and uncharged in nature can be embedded into the sol-gel matrix. Different functionalized/derivatized sol-gel precursors can be used to prepare sol-gel glasses with different physical properties, such as pore size and surface charge. The pore size may be selected by choosing an appropriate sol-gel precursor. For example, to obtain larger pores, tetramethylorthosilicate may be used as the precursor instead of tetraethylorthosilicate indicated above.

Mixture 13 may be prepared as follows. Micron or submicron sized chromatographic particles, such as octadecylsilica may be added to a solution of water, alcohol, acid (optional) or base (optional) and a metal oxide source. The metal oxide source may include a silicate, titanate or zirconate. The resulting solution or mixture 13 formed is injected by syringe into a column and heated overnight. No pre-fabricated frits is required.

Instead of using a syringe to inject the mixture 13 into a channel as described above in reference to FIG. 1, the mixture 13 may be introduced by means of a pressure differential as illustrated in FIG. 6, which is a cross-sectional view of a tube 12 along a longitudinal axis. As shown in FIG. 6, a pressure differential is applied between the inlet end 12*a* and outlet end 12*b*, such as by means of a pump (not shown), in order to introduce a mixture 53 of water, alcohol, acid (optional) or base (optional) and a metal oxide source, without chromatographic particles embedded therein, followed by a mixture 13 of chromatographic particles with a solution such as solution 53, which is again followed by solution 53 to fill tube 12. Solution 53 and mixture 13 are then treated in the manner described above in reference to FIG. 5 to remove the volatile components and to form a porous sol-gel throughout the column 12. Only the section 12*d* of the tube containing the porous sol-gel glass with chromatographic particles embedded therein is used for chromatographic separation. The remaining sections of the tube next to section 12*d* contain a porous sol-gel glass containing no chromatographic particles and, therefore, do not scatter light used for detection, so that the scheme illustrated in FIG. 4 above may be used for detecting separated sample components in a similar manner employing the column of FIG. 6 that has been filled by a porous glass. The column 150 of FIG. 6 is advantageous in that the entire tube is filled by the porous sol-gel glass so that there will no significant pressure differential between the fluid in the porous glass in section 12*d* and that in the porous glass in the remaining sections of the tube. This enhances separation performance.

The pressure differential between the inlet and outlet ends 12*a*, 12*b* may be created in many ways, such as by pushing (i.e. by increasing pressure) the mixtures 53, 13 into the inlet end 12*a*, or by reducing the gas pressure at outlet end 12*b* to draw in solution 53 and mixture 13 as described (since such solution and mixture are under the higher atmospheric pressure at end 12*a*), by means of a pump (not shown). The inlet end 12*a* may also be placed at a higher elevation compared to outlet end 12*b* so that solution 53 and mixture 13 may be introduced by hydrostatic pressure differential.

The packed "fritless" column columns 12 will facilitate the analysis of complex mixtures that may contain charged and/or uncharged compounds. The separation of a mixture of uncharged organic compounds has been demonstrated using a column packed in this manner. Advantages of the disclosed method include (i) easy and rapid injection of the hydrolysis reaction solution into the column, (ii) the elimination of inlet and outlet frit fabrication, (iii) incorporation of charged or uncharged chromatographic materials in the sol-gel matrix, (iv) UV transparency of the sol-gel glass, (v) potential for automation of many samples, and (vi) potential for large-scale preparative use. This results in a total column preparation time of approximately 24 hours and avoids the use of high pressures for post-column conditioning. The use of high voltages is also avoided during column preparation. This system is superior to both the electrokinetic and slurry packing methods.

Instead of using a sol-gel process as described above, other types of polymerization processes may be used, such as that described in the article "Macroporous Polyacrylamide/Poly(ethylene glycol) Matrixes as Stationary Phrases in Capillary Electrochromatography," by Anders Palm and Milos V. Novotny, *Analytical Chemistry*, Vol. 69, No. 22, Nov. 15, 1997, pp. 4499–4507; or the articles by P. G. Righetti, B. C. W. Brost and R. S. Snyder, in *J. Biochem. Biophys. Methods*, 1981, No. 4, pp. 347–363, and by P. G. Righetti, S. Caglio, S. Saracchi and M. Quaroni in *Electrophoresis*, 1992, No. 13, pp. 587–595. As described in these three articles, a porous matrix may be formed by polymerizing a solution of a monomer and a cross-linking reagent or initiator. If said solution is mixed with chromatographic particles and such mixture is used instead of mixture 13 to form the porous matrix with chromatographic particles embedded therein, such matrix may also be used in a separation column for separating a sample into its components in the manner described above. When such a mixture is polymerized, the matrix forms a secure bond to the inner wall of the separation channel so that no frit is necessary to keep the matrix in place. The pores formed are big enough to permit diffusion species but small enough to prevent significant leaching of the chromatographic particles trapped therein. The porous matrix without the particles is transparent to radiation so that the configuration of FIG. 6 described above may be used, where the entire tube is filled with the porous matrix but only a section of the matrix is embedded with chromatographic particles. In this manner, the separated components may be detected downstream from the particles by a detector in a known manner, such as by means of laser induced fluorescence detection. The above-described method for introducing the mixture 13 may also be used for introducing a mixture of the particles with other types of monomers and cross-linking reagents (optional), such as acrylamide or ethylene glycol and an optional base or acid acting as a crosslinking reagnet.

A porous matrix (whether or not embedded with particles) may be formed by heating or supplying radiation to a solution of a monomer such as acrylamide or ethyleneglycol and a cross-linking reagent (optional) such as a base or acid to form a macroporous polyacrylamide or poly(ethylene glycol) matrix. The polymerization is achieved thermally or by photochemistry. In reference to the article by Palm and Novotny, since chromatographic particles are used in this invention for sample separation, there is no need in this invention to include alkyl ligands as described in the Palm and Novotny article. Polymerization techniques different from the above may also be used for forming the porous matrix; such and other variations are within the scope of the invention.

While the invention has been described above by reference to various embodiments, it will be understood that different changes and modifications may be made without departing from the scope of the invention, which is to be defined only by the appended claims and the equivalents thereof.

What is claimed is:

1. An separation column comprising:
  a capillary separation channel having a channel wall; and
  a separation medium in the channel, said medium including a porous matrix attached to the channel wall and micron or submicron sized chromatographic particles embedded in the matrix forming a packed channel, said channel having no frit therein, said matrix including a glass.

2. The column of claim 1, said column having an IC internal dimension in the range of between 5 and 5,000 microns.

3. The column of claim 1, said channel having an elongated cross-section.

4. The column of claim 1, said column having a first portion that is filled with said separation medium and a second portion adjacent to said first portion that transmits radiation.

5. The column of claim 4, wherein said second portion does not contain said separation medium.

6. The column of claim 1, wherein said matrix has pores therein large enough for passage of neutral and charged species but too small for passage of the chromatographic particles.

7. The column of claim 1, said particles being larger than 0.2 micron in dimensions.

8. The column of claim 1, said particles being a mixture of different types of particles of different sizes.

9. The column of claim 1, wherein said glass includes a silicate, titanate or zirconate.

10. The column of claim 1, said column being filled with a porous matrix, said matrix having embedded therein chromatographic particles in only a section of the column.

11. An apparatus for separating a sample into its components, comprising:
  a capillary separation channel having a channel wall;
  a separation medium in the channel, said medium including a porous matrix attached to the channel wall and micron or submicron sized chromatographic particles embedded in the matrix, forming a packed channel, said channel having no frit therein, said matrix including a glass; and
  a device causing a fluid containing a sample present in the channel to flow and the sample to separate.

12. The apparatus of claim 11, said channel being a capillary having an internal dimension in the range of between 5 and 300 microns.

13. The apparatus of claim 11, said channel having a first section that is filled with said separation medium and a second section adjacent to said first portion that transmits radiation.

14. The apparatus of claim 13, wherein said second section does not contain said separation medium.

15. The apparatus of claim 13, said second section containing a porous matrix not embedded with chromatographic particles.

16. The apparatus of claim 15, said channel filled with a porous matrix.

17. The apparatus of claim 13, said device causing the sample to pass through the second section, said apparatus further comprising:
  means for applying radiation to the sample in the second section; and
  means for detecting radiation from the second section to detect components of the sample passing through the second section.

18. The apparatus of claim 11, said causing means applying an electric field along the channel, so that the sample separates by electrophoresis and chromatography.

19. The apparatus of claim 11, said device applying a pressure differential along the channel, so that the sample separates by chromatography.

20. The apparatus of claim 11, said causing means applying both an electric field and a pressure differential along the channel, so that the sample separates by electrophoresis and chromatography.

21. The apparatus of claim 11, wherein said matrix has pores therein large enough for passage of neutral and charged species but too small for passage of the chromatographic particles.

22. The apparatus of claim 11, said particles being larger than 0.2 micron in dimensions.

23. The apparatus of claim 11, wherein said glass includes a silicate, titanate or zirconate.

24. The apparatus of claim 11, said column being filled with a porous matrix, said matrix having embedded therein chromatographic particles in only a section of the column.

25. A separation column comprising:
  a capillary separation channel having a channel wall; and
  a separation medium in the channel, said medium including a porous matrix attached to the channel wall and micron or submicron sized chromatographic particles embedded in the matrix forming a packed channel, said matrix including an a glass material.

26. A separation column, useful for separating different species in a sample, comprising:
  a capillary separation channel having a channel wall; and
  a glassy, porous matrix attached to the channel wall, the matrix having micron or submicron sized chromatographic particles embedded in the matrix, the particles adapted to interact with species in the sample and to cause separation of sample species when passed through the matrix.

27. The column as in claim 26 wherein the channel is a capillary having an internal dimension defined by a capillary wall and being from about 5 to about 300 microns.

28. The column as in claim 27 wherein the matrix entirely fills the capillary in at least a first section thereof.

29. The column as in claim 28 wherein attachments between capillary wall, matrix and the particles embedded therein are sufficient to maintain the matrix and embedded particles within the capillary without a frit.

* * * * *